United States Patent [19]

Wepplo et al.

[11] Patent Number: 5,256,629
[45] Date of Patent: Oct. 26, 1993

[54] 3-(SUBSTITUTED KETONE AND ALCOHOL)-2-(2-IMIDAZOLIN-2-YL) PYRIDINE COMPOUNDS USEFUL AS HERBICIDAL AGENTS

[75] Inventors: Peter J. Wepplo, Princeton, N.J.; Alvin D. Crews, Yardley, Pa.

[73] Assignee: American Cyanamid Company, Stamford, Conn.

[21] Appl. No.: 893,180

[22] Filed: Jun. 3, 1992

[51] Int. Cl.$^5$ .................. A01N 43/40; C07D 213/30
[52] U.S. Cl. ..................................... 504/130; 546/278
[58] Field of Search ..................... 71/92; 546/278; 504/130

[56] References Cited

U.S. PATENT DOCUMENTS 4,798,619  1/1989  Los ............................................. 71/92

Primary Examiner—C. Warren Ivy
Assistant Examiner—Zinna N. Davis
Attorney, Agent, or Firm—John W. Hogan, Jr.

[57] ABSTRACT 3-(Substituted ketone and alcohol)-2-(2-imidazolin-2-yl)pyridine and quinoline compounds which are effective in the control of undesirable plant species are described. Also described are a method for the herbicidal use of the compounds and a method for their preparation.

9 Claims, No Drawings

3-(SUBSTITUTED KETONE AND ALCOHOL)-2-(2-IMIDAZOLIN-2-YL) PYRIDINE COMPOUNDS USEFUL AS HERBICIDAL AGENTS

BACKGROUND OF THE INVENTION

Weeds cause tremendous global economic losses by reducing crop yields and lowering crop values. In the United States, crops must compete with 1,800 different weeds. Accordingly, there is an ongoing search in the art to create more effective and/or more selective herbicidal agents.

U.S. Pat. No. 4,798,619 discloses a variety of effective herbicidal agents including 3-(benzoyl and hydroxyalkyl)-2-(2-imidazolin-2-yl)pyridine and quinoline compounds. While these compounds and other known herbicides may be effective herbicidal agents, there are increasing concerns with the environment and therefore increasing efforts have been undertaken to find more potent herbicides, i.e. those herbicides which can be applied at a lower rate, but still give the same or better control of a broad spectrum of undesirable plant species.

It is an object of the present invention to provide compounds that are highly effective for controlling undesirable plant species.

SUMMARY OF THE INVENTION

The present invention describes 3-(substituted ketone and alcohol)-2-(2-imidazolin-2-yl)pyridine and quinoline compounds that are highly effective herbicidal agents useful for the control of undesirable plant species and methods for their preparation.

The 3-(substituted ketone)-2-(2-imidazolin-2-yl)pyridine and quinoline compounds of the present invention are illustrated as formula I and the 3-(substituted alcohol)-2-(2-imidazolin-2-yl)pyridine and quinoline compounds of the present invention are illustrated as formula II:

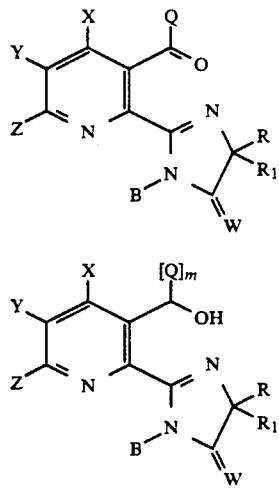

wherein
R is $C_1$-$C_4$ alkyl;
$R_1$ is $C_1$-$C_4$ alkyl or $C_3$-$C_6$ cycloalkyl; and when R and $R_1$ are taken together with the carbon to which they are attached they may represent $C_3$-$C_6$ cycloalkyl optionally substituted with methyl;

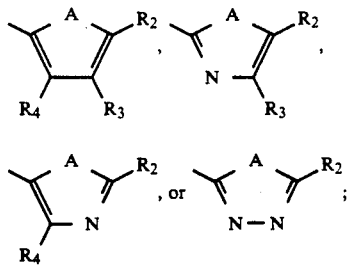

$R_2$, $R_3$ and $R_4$ are each independently hydrogen, halogen, $C_1$-$C_4$ alkyl, $C_1$-$C_4$ alkoxy, $C_1$-$C_4$ haloalkoxy or phenyl optionally substituted with one or two halogen atoms, $C_1$-$C_4$ alkyl or haloalkyl groups or $C_1$-$C_4$ alkoxy or haloalkoxy groups.
m is an integer of 1 or 2;
A is O, S, or $NR_5$; provided that when m is 2, A is O;
$R_5$ is $C_1$-$C_4$ alkyl;
B is hydrogen, $COR_6$ or $SO_2R_7$;
$R_6$ is $C_1$-$C_{11}$ alkyl, chloromethyl or phenyl optionally substituted with one chloro, one nitro or one methoxy group;
$R_7$ is $C_1$-$C_4$ alkyl or phenyl optionally substituted with one methyl group;
W is O or S;
X is hydrogen, halogen or methyl;
Y and Z are each independently hydrogen, halogen, $C_1$-$C_6$ alkyl, $C_1$-$C_4$ alkoxymethyl, $C_1$-$C_6$ alkoxy, $C_1$-$C_4$ alkylthio, phenoxy, $C_1$-$C_4$ haloalkyl, nitro, cyano, $C_1$-$C_4$ alkylsulfonyl or phenyl optionally substituted with one $C_1$-$C_4$ alkyl, $C_1$-$C_4$ alkoxy or halogen; and, when taken together, Y and Z may form a ring in which YZ are represented by the structure: —$(CH_2)_n$—, where n is an integer selected from 3 and 4; or

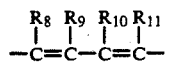

where $R_8$, $R_9$, $R_{10}$ and $R_{11}$ are each independently hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, nitro, cyano, phenyl, phenoxy, amino, chlorophenyl, methylphenyl, or phenoxy substituted with one chloro, trifluoromethyl, nitro or methyl group, with the proviso that only one of $R_8$, $R_9$, $R_{10}$ or $R_{11}$, may represent a substituent other than hydrogen, halogen, $C_1$-$C_4$ alkyl or $C_1$-$C_4$ alkoxy;
and when R and $R_1$ are not the same, the optical isomers thereof.

While 3-(benzoyl and hydroxyalkyl)-2-(2-imidazolin-2-yl)pyridine and quinoline compounds have been known, surprisingly, the 3-(substituted ketone and alcohol)-2-(2-imidazolin-2-yl)pyridine and quinoline compounds of the present invention give better control of undesirable plant species at low rates.

DETAILED DESCRIPTION OF THE INVENTION

Surprisingly, it has been found that the formula I and formula II compounds of this invention are more potent herbicidal agents at lower rates, especially postemergence, than the 3-(benzoyl and hydroxyalkyl)-2-(2-imidazolin-2-yl)pyridine and quinoline compounds known in the art. Advantageously, compounds of the present invention also control a wider variety of undesirable plant species at those lower rates than the 3-(benzoyl and hydroxyalkyl)-2-(2-imidazolin-2-yl)pyridine and quinoline compounds. Naturally, a low rate is desirable because it means increased safety for the farmer and the environment. Preferred 3-(substituted ketone and alcohol)-2-(2-imidazolin-2-yl)pyridine and quinoline compounds of the present invention that are especially effective in the control of undesirable plant species are illustrated as formulas III and IV:

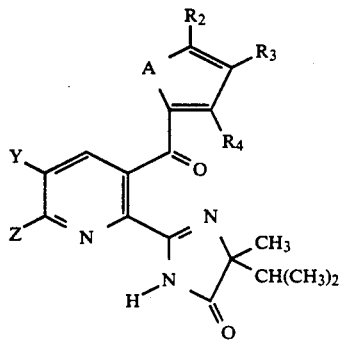

(III)

Y and Z are each independently hydrogen, halogen, $C_1-C_6$ alkyl, $C_1-C_4$ alkoxymethyl or $C_1-C_6$ alkoxy, and when taken together, Y and Z may form a ring in which YZ are represented by the structure:

—CH=CH—CH=CH—.

Expecially preferred compounds of the present invention are formula III compounds wherein $R_3$ is hydrodgen and $R_2$ and $R_4$ are independently hydrogen, halogen, $C_1-C_4$ alkyl, $C_1-C_4$ alkoxy or $C_1-C_4$ haloalkoxy.

Exemplary of halogen hereinabove are fluorine, chlorine, bromine and iodine. The term "haloalkyl" is defined as a compound of the following formula $C_pH_qM_r$ where M is halogen and p, q and r are integers such that $q+r =2p+1$. The term "haloalkoxy" is defined as a compound of the following formula $C_pH_qM_rO$ where M is halogen and p, q and r are integers such that $q+r =2p+1$.

Compounds of formula I and formula II, wherein m is 2, may be prepared as shown in Flow Diagram I.

FLOW DIAGRAM I

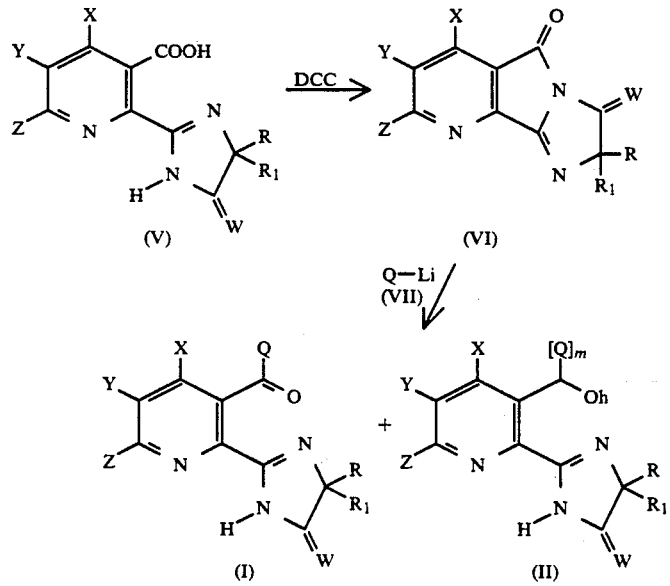

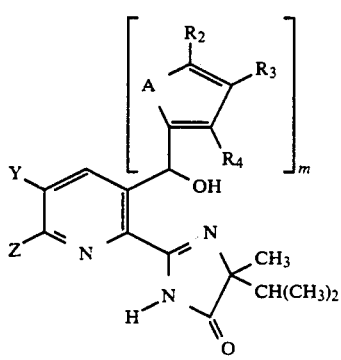

(IV)

wherein $R_2$, $R_3$, $R_4$ and m are as described above; A is O or S;

The appropriately substituted formula V 2-(2-imidazolin-2-yl)pyridine or quinoline acid is reacted with about one equivalent of a dehydrating agent such as diisopropylcarbodiimide or dicyclohexylcarbodiimide (DCC) in the presence of an aprotic solvent such as methylene chloride or tetrahydrofuran preferably at a temperature between about 20° C. to 32° C. to form the formula VI compound. Said formula VI compound is then reacted with one or more equivalents of the appropriately substituted formula VII lithium agent in the presence of an organic solvent such as tetrahydrofuran preferably at a temperature between about −78° C. to 30° C. to obtain the desired formula I and formula II compounds.

Compounds of formula II wherein m is 1 may be prepared as shown in Flow Diagram II.

FLOW DIAGRAM II

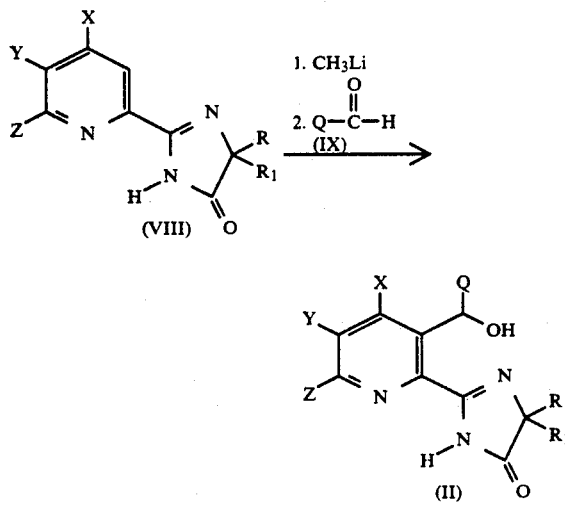

The appropriately substituted formula VIII imidazolinone compound is reacted with at least about 2.0 molar equivalents of a $C_1$–$C_4$ alkyl lithium in the presence of an inert solvent such as tetrahydrofuran preferably at a temperature between about $-80°$ C. to $0°$ C. The thus-formed salt is then treated with at least about 1.0 molar equivalents of the appropriately substituted formula IX aldehyde compound in an inert solvent such as tetrahydrofuran preferably at a temperature between about $-80°$ C. to $40°$ C. to obtain the desired formula II compound.

Advantageously, the thus-formed formula II compound wherein m is 1 is reacted with an oxidizing agent such as manganese(IV) oxide in the presence of an inert organic solvent such as chloroform preferably at a temperature between about $20°$ C. to $80°$ C. to give a formula I compound. The reaction scheme is illustrated in Flow Diagram III.

FLOW DIAGRAM III

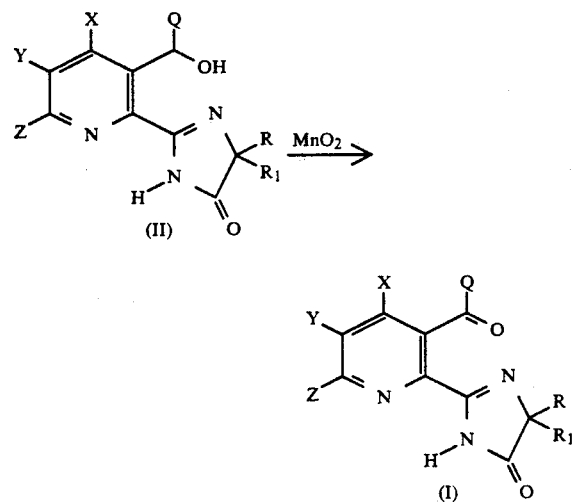

Compounds of formulas V, VI and VIII and methods of preparation thereof are described in U.S. Pat. No. 4,798,619.

Preparation of formula I and formula II N-substituted derivatives, wherein B is $COR_6$ or $SO_2R_7$; m is 2; and R, $R_1$, Q, $R_2$, $R_3$, $R_4$, A, $R_5$, W, X, Y and Z are as described above, can be achieved by reaction of the appropriately substituted formula I or formula II compound wherein B is hydrogen with an excess of acyl halide, acyl anhydride or sulfonyl halide, alone or in a solvent such as pyridine or toluene at a temperature between about $50°$ C. to $125°$ C.

Formula II compounds wherein m is 1 and B is $COR_6$ or $SO_2R_7$ may be prepared by reducing formula I compounds wherein B is $COR_6$ or $SO_2R_7$ with a reducing agent such as sodium borohydride.

The formula I 3-(substituted ketone)-2-(2-imidazolin-2-yl)pyridines and quinolines and the formula II 3-(substituted alcohol)-2-(2-imidazolin-2-yl)pyridines and quinolines of the present invention are effective herbicidal agents useful for the control of a wide variety of herbaceous and woody, annual and perennial, monocotyledonous and dicotyledonous plants. These compounds are effective for controlling weeds native to both dry land and wet land areas. The compounds are effective in controlling the above-said plants when applied to the foliage thereof or to soil or water containing seeds or other propagating organs of said plants such as stolons, tubers or rhizomes, at rates of from about 0.016 to 4.0 kg/ha and preferably from about 0.125 to 4.0 kg/ha.

Advantageously, it has been found that the compounds of this invention are best suited for use as broad spectrum herbicides, especially when applied postemergence to the locus in which weed control is desired. This is not to say, however, that all of the compounds of this invention are non-selective. In fact, some of the compounds of this invention are selective in leguminous crops, such as soybeans.

The formula I and formula II compounds of this invention may be applied to crops in the form of a solid or liquid herbicidal composition, comprising a herbicidally effective amount of the formula I or formula II compound dispersed or dissolved in an inert solid or liquid carrier. The formulations may be applied as preemergence or postemergence treatments.

Advantageously, the formula I and formula II compounds can be formulated as emulsifiable concentrates, wettable powders, granular formulations, flowable concentrates and the like.

In order to facilitate a further understanding of the invention, the following examples are presented to illustrate more specific details thereof. The invention is not to be limited thereby except as defined in the claims.

EXAMPLE 1

Preparation of
4-Isopropyl-4-methyl-2-[5-methyl-3-(2-thenoyl)-2-pyridyl]-2-imidazolin-5-one

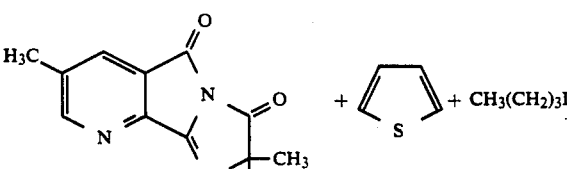

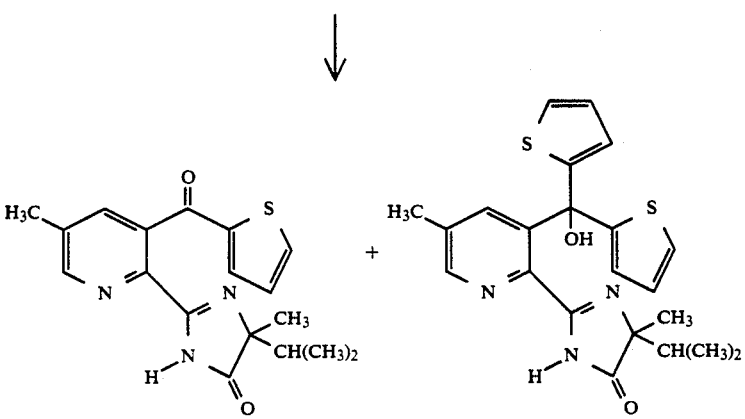

A solution of thiophene (3.3 mL) in anhydrous tetrahydrofuran (150 mL) is cooled to −78° C. and treated with a 2.5 molar solution of n-butyllithium in hexanes (16.8 mL) for 30 minutes. 2-Isopropyl-2,7-dimethyl-5H-imidazo[1′,2′:1,2]pyrrolo[3,4-b]pyridine-3(2H),5-dione (10.19 g, 0.0396 mol) is added and the reaction mixture is stirred at room temperature for three days, diluted with water and extracted with ethyl acetate. The combined organic extracts are washed with brine, dried (Na₂SO₄) and concentrated in vacuo to obtain a colorless oil. Chromatography of the oil using silica gel and a 30% hexane in diethyl ether mixture gives 2-[3-(hydroxydi-2-thienylmethyl)-5-methyl-2-pyridyl]-4-isopropyl-4-methyl-2-imidazolin-5-one as a white solid (1.0 g, mp 190°-191° C.) and 4-isopropyl-4-methyl-2-[5-methyl-3-(2-thenoyl)-2-pyridyl]-2-imidazolin-5-one as a white solid (0.45 g, mp 168°-170° C.).

Using essentially the same procedure and employing the appropriately substituted 5H-imidazo-[1′,2′:1,2]pyrrolo[3,4-b]pyridine-3(2H),5-dione and the appropriate thiophene or furan, the following compounds are obtained.

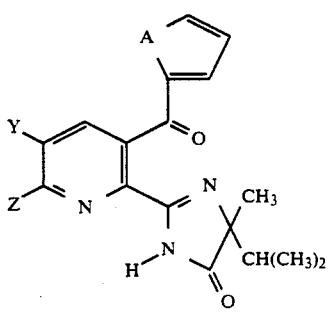

| A | Y | Z | mp° |
|---|---|---|---|
| O | H | H | 145-146 |
| S | H | H | 144-145 |
| O | CH₃ | H | 159-160 |
| O | C₂H₅ | H | 108-110 |
| S | C₂H₅ | H | 153-154 |
| O | CH₂OCH₃ | H | 123-125 |
| S | CH₂OCH₃ | H | 144-147 |
| S | —CH=CH—CH=CH— | | 235-238 |

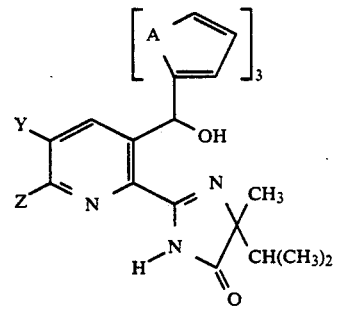

| A | Y | Z | mp° |
|---|---|---|---|
| O | H | H | 138-139 |
| O | CH₃ | H | 133-134 |
| O | CH₂OCH₃ | H | 138-140 |

EXAMPLE 2

Preparation of
2-[3-(α-Hydroxy-5-methyl-2-thenyl)-5-methyl-2-pyridyl]-4-isopropyl-4-methyl-2-imidazolin-5-one

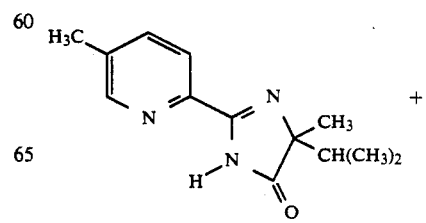

-continued

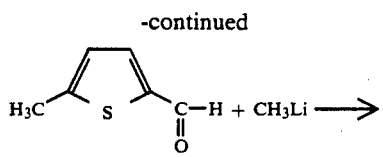

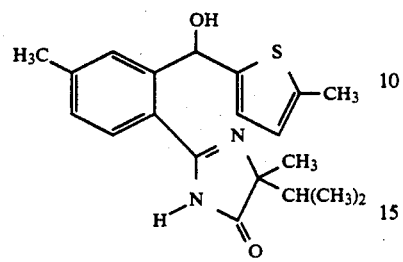

A stirred solution of 4-isopropyl-4-methyl-2-(5-methyl-2-pyridyl)-2-imidazolin-5-one (10.0 g, 0.043 mol) in anhydrous tetrahydrofuran (200 mL) is cooled to −78° C. and treated with a 1.5 molar solution of methyl lithium in diethyl ether (60.6 mL). The resultant suspension is stirred at −78° C. for 30 minutes and at 0° C. for 30 minutes. The reaction mixture is recooled to −78° C. and 5-methyl-2-thiophenecarboxaldehyde (15.35 g, 0.043 mol) is added dropwise. After 30 minutes, the cooling bath is removed and the reaction mixture is stirred at room temperature overnight then diluted with water. The aqueous mixture is acidified to pH 6 with acetic acid and extracted with diethyl ether. The combined organic extracts are washed with water, dried (Na$_2$SO$_4$) and concentrated in vacuo to obtain an orange oil. Chromatography of the oil using silica gel and a 20% diethyl ether in methylene chloride mixture gives a yellow oil which is triturated with diethyl ether to obtain the title product as a white solid (2.0 g, mp 147°–148° C.)

Using essentially the same procedure and employing the appropriately substituted 2-(2-pyridyl)-2-imidazolin-5-one and the appropriate 2-thiophenecarboxaldehyde or 2-furaldehyde, the following compounds are obtained:

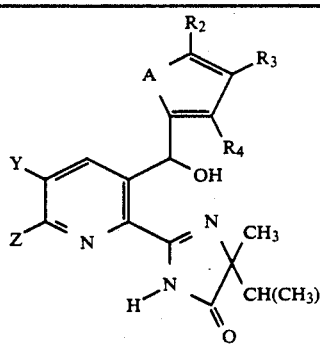

| A | Y | Z | R$_2$ | R$_3$ | R$_4$ | mp °C. |
|---|---|---|---|---|---|---|
| O | H | H | H | H | H | 151–158 |
| O | H | H | CH$_3$ | H | H | glass |
| S | H | H | H | H | CH$_3$ | glass |
| O | CH$_3$ | H | H | H | H | 163–165 |
| O | CH$_3$ | H | CH$_3$ | H | H | 130–135 |
| O | CH$_3$ | H | C$_2$H$_5$ | H | H | oil |
| S | CH$_3$ | H | H | H | CH$_3$ | 123–127 |
| O | C$_2$H$_5$ | H | H | H | H | 115–121 |
| S | C$_2$H$_5$ | H | H | H | H | 140–155 |
| O | C$_2$H$_5$ | H | CH$_3$ | H | H | liquid |
| S | C$_2$H$_5$ | H | CH$_3$ | H | H | 120–122 |

-continued

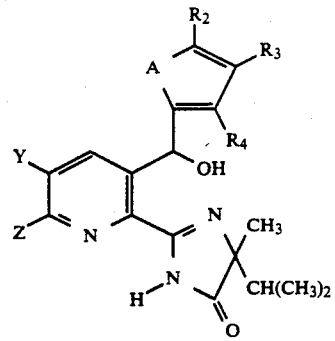

| A | Y | Z | R$_2$ | R$_3$ | R$_4$ | mp °C. |
|---|---|---|---|---|---|---|
| O | C$_2$H$_5$ | H | C$_2$H$_5$ | H | H | 118–121 |
| S | C$_2$H$_5$ | H | H | H | CH$_3$ | 121–123 |
| S | C$_2$H$_5$ | H | Cl | H | H | 131–133 |
| S | —CH=CH—CH=CH— | H | H | | 168–170 |
| S | —CH=CH—CH=CH— | CH$_3$ | H | H | 179–185 |

EXAMPLE 3

Preparation of 4-Isopropyl-4-methyl-2-[5-methyl-3-(5-methyl-2-thenoyl)-2-pyridyl]-2-imidazolin-5-one

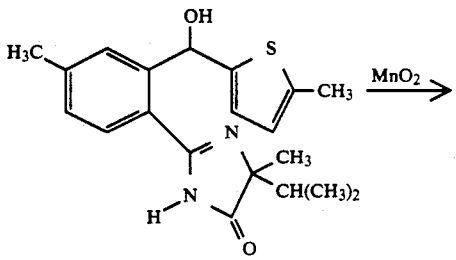

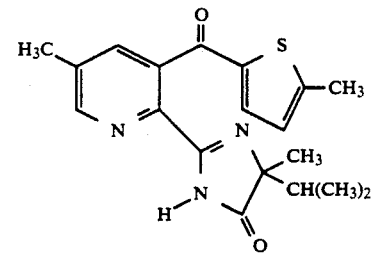

A solution of 2-[(3-(α-hydroxy-5-methyl-2-thenyl)-5-methyl-2-pyridyl]-4-isopropyl-4-methyl-2-imidazolin-5-one (1.35 g, 0.0038 mol) in chloroform (75 mL) is treated with manganese dioxide (10 g, 0.12 mol) and heated to 60° C. After 10 minutes, additional manganese dioxide (10 g) is added and the reaction mixture is stirred at 60° C. for 2 hours, cooled to room temperature and filtered through diatomaceous earth. The filtrate is concentrated in vacuo to obtain a residue which is crystallized from diethyl ether to give the title product as a white solid (1.2 g, mp 173°–175° C.).

Using essentially the same procedure and employing the appropriately substituted 2-{3-[α-hydroxy-2-(thenyl or furfuryl)]-2-pyridyl}-2-imidazolin-5-one, the following compounds are obtained:

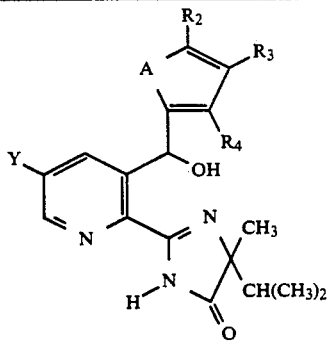

| A | Y | $R_2$ | $R_3$ | $R_4$ | mp °C. |
|---|---|---|---|---|---|
| S | H | H | H | $CH_3$ | 150-152 |
| S | $CH_3$ | H | H | $CH_3$ | 173-178 |
| O | $C_2H_5$ | $CH_3$ | H | H | 106-108 |
| S | $C_2H_5$ | $CH_3$ | H | H | 140-142 |
| S | $C_2H_5$ | H | H | $CH_3$ | glass |
| S | $C_2H_5$ | Cl | H | H | glass |

EXAMPLE 4

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.125 to 4.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this preemergence herbicidal evaluation and in the post-emergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared To Check |
|---|---|---|
| 9 | Complete Kill | 100 |
| 8 | Approaching Complete kill | 91-99 |
| 7 | Good Herbicidal Effect | 80-90 |
| 6 | Herbicidal Effect | 65-79 |
| 5 | Definite Injury | 45-64 |
| 4 | Injury | 30-44 |
| 3 | Moderate Effect | 16-29 |
| 2 | Slight Effect | 6-15 |
| 1 | Trace Effect | 1-5 |
| 0 | No Effect | 0 |

PLANT SPECIES EMPLOYED IN HERBICIDAL EVALUATIONS

| Header Abb. | Common Name | Scientific Name |
|---|---|---|
| Barnydgr | Barnyardgrass | ECHINOCHLOA CRUS-GALLI, (L) BEAU |
| Foxtail Sp | Foxtail Spp. | SETARIA SPP. |
| Wild Oats | Oat, Wild | AVENA FATUA, L. |
| Quackgrass | Quackgrass | AGROPYRON REPENS, (L) BEAUV |
| Fld Bindwd | Bindweed, Field | CONVOLVULUS ARVENSIS, (RHIZOME) L. |
| Mrnglry Sp | Morningglory | IPOMOEA SPP. |
| Wild Mustd | Mustard, Wild | BRASSICA KABER, (DC) L. C. WHEELR |
| Velvetleaf | Velvetleaf | ABUTILON THEOPHRASTI, MEDIC. |
| Wht Fenman | Wheat, Fenman | TRITICUM AESTIVUM, FENMAN |
| Corn Field, | Corn, Field | ZEA MAYS, L. |
| Cotton | Cotton | GOSSYPIUM HIRSUTUM, L. |
| Soybean | Soybean | GLYCINE MAX |

COMPOUNDS EVALUATED AS HERBICIDAL AGENTS

| Compound No. | |
|---|---|
| 1 | 2-[3-(2-Furoyl)-2-pyridyl]-4-isopropyl-4-methyl-2-imidazolin-5-one |
| 2 | 4-Isopropyl-4-methyl-2-[3-(3-methyl-2-thenoyl)-2-pyridyl]-2-imidazolin-5-one |
| 3 | 4-Isopropyl-4-methyl-2-[3-(2-thenoyl)-2-pyridyl]-2-imidazolin-5-one |
| 4 | 2-[3-(2-Furoyl)-5-methyl-2-pyridyl]-4-isopropyl-4-methyl-2-imidazolin-5-one |
| 5 | 4-Isopropyl-4-methyl-2-[5-methyl-3-(2-thenoyl)-2-pyridyl]-2-imidazolin-5-one |
| 6 | 4-Isopropyl-4-methyl-2-[5-methyl-3-(5-methyl-2-thenoyl)-2-pyridyl]-2-imidazolin-5-one |
| 7 | 4-Isopropyl-4-methyl-2-[5-methyl-3-(3-methyl-2-thenoyl)-2-pyridyl]-2-imidazolin-5-one |
| 8 | 2-[5-Ethyl-3-(2-furoyl)-2-pyridyl]-4-isopropyl-4-methyl-2-imidaozolin-5-one |
| 9 | 2-[5-Ethyl-3-(2-thenoyl)-2-pyridyl]-4-isopropyl-4-methyl-2-imidazolin-5-one |
| 10 | 2-[5-Ethyl-3-(5-methyl-2-furoyl)-2-pyridyl]-4-isopropyl-4-methyl-2-imidazolin-5-one |
| 11 | 2-[5-Ethyl-3-(5-methyl-2-thenoyl)-2-pyridyl]-4-isopropyl-4-methyl-2-imidazolin-5-one |
| 12 | 2-[5-Ethyl-3-(3-methyl-2-thenoyl)-2-pyridyl]-4-isopropyl-4-methyl-2-imidazolin-5-one |
| 13 | 2-[3-(5-Chloro-2-thenoyl)-5-ethyl-2-pyridyl]-4-isopropyl-4-methyl-2-imidazolin-5-one |
| 14 | 2-[3-(2-Furoyl)-5-(methoxymethyl)-2-pyridyl]-4-isopropyl-4-methyl-2-imidazolin-5-one |
| 15 | 4-Isopropyl-2-[5-(methoxymethyl)-3-(2-thenoyl)-2-pyridyl]-4-methyl-2-imidazolin-5-one |
| 16 | 4-Isopropyl-4-methyl-2-[3-(2-thenoyl)-2-quinolyl]-2-imidazolin-5-one |
| 17 | 2-[3-(α-Hydroxyfurfuryl)-2-pyridyl]-4-isopropyl-4-methyl-2-imidazolin-5-one |
| 18 | 2-[3-(α-Hydroxy-5-methylfurfuryl)-2-pyridyl]-4-isopropyl-4-methyl-2-imidazolin-5-one |
| 19 | 2-[3-(α-Hydroxy-3-methyl-2-thenyl)-2-pyridyl]-4-isopropyl-4-methyl-2-imidazolin-5-one |
| 20 | 2-[3-(α-Hydroxyfurfuryl)-5-methyl-2-pyridyl]-4-isopropyl-4-methyl-2-imidazolin-5-one |
| 21 | 2-[3-(α-Hydroxy-5-methylfurfuryl)-5-methyl-2-pyridyl]-4-isopropyl-4-methyl-2-imidazolin-5- |

COMPOUNDS EVALUATED AS HERBICIDAL AGENTS

| Compound No. | |
|---|---|
| | one |
| 22 | 2-[3-(α-Hydroxy-5-methyl-2-thenyl)-5-methyl-2-pyridyl]-4-isopropyl-4-methyl-2-imidazolin-5-one |
| 23 | 2-[3-(5-Ethyl-α-Hydroxyfurfuryl)-5-methyl-2-pyridyl]-4-isopropyl-4-methyl-2-imidazolin-5-one |
| 24 | 2-[3-(α-Hydroxy-3-methyl-2-thenyl)-5-methyl-2-pyridyl]-4-isopropyl-4-methyl-2-imidazolin-5-one |
| 25 | 2-[5-Ethyl-3-(α-hydroxyfurfuryl)-2-pyridyl]-4-isopropyl-4-methyl-2-imidazolin-5-one |
| 26 | 2-[5-Ethyl-3-(α-hydroxy-2-thenyl)-2-pyridyl]-4-isopropyl-4-methyl-2-imidazolin-5-one |
| 27 | 2-[5-Ethyl-3-(α-hydroxy-5-methylfurfuryl)-2-pyridyl]-4-isopropyl-4-methyl-2-imidazolin-5-one |
| 28 | 2-[5-Ethyl-3-(α-hydroxy-5-methyl-2-thenyl)-2-pyridyl]-4-isopropyl-4-methyl-2-imidazolin-5-one |
| 29 | 2-[5-Ethyl-3-(5-ethyl-α-hydroxyfurfuryl)-2-pyridyl]-4-isopropyl-4-methyl-2-imidazolin-5-one |
| 30 | 2-[5-Ethyl-3-(α-hydroxy-3-methyl-2-thenyl)-2-pyridyl]-4-isopropyl-4-methyl-2-imidazolin-5-one |
| 31 | 2-[3-(5-Chloro-α-hydroxy-2-thenyl)-5-ethyl-2-pyridyl]-4-isopropyl-4-methyl-2-imidazolin-5-one |
| 32 | 2-[3-(α-Hydroxy-2-thenyl)-2-quinolyl]-4-isopropyl-4-methyl-2-imidazolin-5-one |
| 33 | 2-[3-(α-Hydroxy-5-methyl-2-thenyl)-2-quinolyl]-4-isopropyl-4-methyl-2-imidazolin-5-one |
| 34 | 2-{3-[(di-2-Furyl)hydroxymethyl]-2-pyridyl}-4-isopropyl-4-methyl-2-imidazolin-5-one |
| 35 | 2-[3-(di-2-Furylhydroxymethyl)-5-methyl-2-pyridyl]-4-isopropyl-4-methyl-2-imidazolin-5-one |
| 36 | 2-[3-(di-2-Furylhydroxymethyl)-5-(methoxymethyl)-2-pyridyl]-4-isopropyl-4-methyl-2-imidazolin-5-one |

TABLE I

Preemergence Herbicidal Evaluation of Test Compounds

| Compound No. | Rate (kg/ha) | Barn-yardgr | Foxtail Sp | Wild oats | Quack grass | Fld Bindwd | Mrnglry Sp | Wild mustd | Velvet-leaf | Wht Fenman | Corn field | Cotton | Soybean |
|---|---|---|---|---|---|---|---|---|---|---|---|---|---|
| 1 | 4.000 | 8.0 | — | 7.0 | 9.0 | 9.0 | 8.0 | 9.0 | 8.0 | — | — | — | — |
|  | .500 | 7.0 | 9.0 | 9.0 | 9.0 | 9.0 | 9.0 | 9.0 | 9.0 | 9.0 | 9.0 | 9.0 | 8.0 |
|  | .125 | 6.0 | 9.0 | 9.0 | 9.0 | 9.0 | 8.0 | 9.0 | 9.0 | 9.0 | 9.0 | 9.0 | 7.0 |
| 2 | 4.000 | 9.0 | — | 8.0 | 9.0 | 9.0 | 8.0 | 9.0 | 8.0 | — | — | — | — |
|  | .500 | 7.0 | 9.0 | 9.0 | 7.0 | 9.0 | 7.0 | 9.0 | 8.0 | 9.0 | 9.0 | 9.0 | 8.0 |
|  | .125 | 1.4 | 4.0 | 0.0 | 2.0 | 4.0 | 1.7 | 8.0 | 2.0 | 8.0 | 7.0 | 4.0 | 0.0 |
| 3 | 4.000 | 8.0 | — | 7.0 | 9.0 | 9.0 | 7.0 | 9.0 | 8.0 | — | — | — | — |
|  | .500 | 7.0 | 9.0 | 9.0 | 9.0 | 9.0 | 8.0 | 9.0 | 9.0 | 9.0 | 9.0 | 9.0 | 7.0 |
|  | .125 | 5.0 | 5.0 | 7.0 | 9.0 | 9.0 | 5.0 | 9.0 | 9.0 | 7.0 | 4.0 | 7.0 | 4.0 |
| 4 | .500 | 9.0 | 9.0 | 9.0 | 9.0 | 9.0 | 9.0 | 9.0 | 9.0 | 9.0 | 9.0 | 9.0 | 8.0 |
|  | .125 | 6.0 | 7.0 | 9.0 | 0.0 | 9.0 | 6.0 | 9.0 | 8.0 | 6.0 | 8.0 | 8.0 | 8.0 |
| 5 | .500 | 8.0 | 8.0 | 8.0 | 0.0 | 8.0 | 8.0 | 9.0 | 8.0 | 5.0 | 8.0 | 6.0 | 7.0 |
|  | .125 | 0.0 | 2.0 | 0.0 | 0.0 | 0.0 | 0.0 | 8.0 | 2.0 | 0.0 | 0.0 | 0.0 | 0.0 |
| 6 | 4.000 | 8.0 | — | 8.0 | 9.0 | 9.0 | 8.0 | 9.0 | 9.0 | — | — | — | — |
|  | .500 | 5.0 | 4.0 | 1.5 | 1.5 | 4.5 | 4.7 | 4.5 | 4.0 | 1.5 | 2.0 | 3.0 | 2.0 |
|  | .125 | 1.4 | 1.5 | 0.0 | 0.0 | 4.5 | 0.7 | 4.0 | 3.5 | 0.0 | 0.0 | 1.0 | 0.5 |
| 7 | .500 | 8.0 | 9.0 | 3.0 | 2.0 | 9.0 | 8.0 | 9.0 | 9.0 | 0.0 | 2.0 | 8.0 | 2.0 |
|  | .125 | 0.0 | 0.0 | 0.0 | 0.0 | 4.0 | 0.0 | 7.0 | 2.0 | 0.0 | 0.0 | 0.0 | 0.0 |
| 8 | .500 | 8.0 | 8.0 | 8.0 | 9.0 | 9.0 | 7.0 | 9.0 | 8.0 | 6.0 | 7.0 | 7.0 | 0.0 |
|  | .125 | 0.0 | 0.0 | 4.0 | 0.0 | 9.0 | 0.0 | 9.0 | 7.0 | 0.0 | 2.0 | 0.0 | 0.0 |
| 9 | .500 | 6.0 | 2.0 | 4.0 | 9.0 | 9.0 | 0.0 | 9.0 | 5.0 | 1.0 | 2.0 | 3.0 | 0.0 |
|  | .125 | 0.0 | 0.0 | 0.0 | 0.0 | 9.0 | 0.0 | 6.0 | 0.0 | 0.0 | 0.0 | 0.0 | 0.0 |
| 10 | 4.000 | 8.0 | — | 9.0 | 9.0 | 9.0 | 9.0 | 8.0 | 9.0 | 9.0 | — | — | — |
|  | .500 | 8.0 | 9.0 | 9.0 | 9.0 | 9.0 | 8.0 | 9.0 | 9.0 | 8.0 | 8.0 | 9.0 | 2.0 |
|  | .125 | 3.0 | 3.0 | 1.0 | 3.0 | 9.0 | 4.0 | 9.0 | 8.0 | 1.0 | 2.0 | 4.0 | 0.0 |
| 11 | 4.000 | 8.0 | — | 8.0 | 8.0 | 9.0 | 7.0 | 9.0 | 8.0 | — | — | — | — |
|  | .500 | 1.0 | 2.0 | 1.0 | 1.5 | 4.5 | 1.0 | 5.0 | 3.5 | 1.0 | 1.0 | 2.0 | 0.0 |
|  | .125 | 0.0 | 0.0 | 0.0 | 0.0 | 0.0 | 0.0 | 2.0 | 0.5 | 0.0 | 0.0 | 0.0 | 0.0 |
| 12 | .500 | 1.0 | 4.0 | 0.0 | 4.0 | 9.0 | 0.0 | 9.0 | 8.0 | 0.0 | 0.0 | 2.0 | 0.0 |
|  | .125 | 0.0 | 0.0 | 0.0 | 0.0 | 6.0 | 0.0 | 0.0 | 1.0 | 0.0 | 0.0 | 0.0 | 0.0 |
| 13 | .500 | 4.0 | 4.0 | 4.0 | 5.0 | 9.0 | 6.0 | 8.0 | 7.0 | 2.0 | 3.0 | 2.0 | 0.0 |
|  | .125 | 0.0 | 4.0 | 0.0 | 0.0 | 2.0 | 0.0 | 8.0 | 4.0 | 0.0 | 0.0 | — | 0.0 |
| 14 | .500 | 7.0 | 8.0 | 9.0 | 9.0 | 9.0 | 7.0 | 9.0 | 8.0 | 9.0 | 9.0 | 9.0 | 2.0 |
|  | .125 | 0.0 | 2.0 | 7.0 | 6.0 | 4.0 | 0.0 | 7.0 | 4.0 | 8.0 | 7.0 | 0.0 | 0.0 |
| 15 | .500 | 4.0 | 8.0 | 9.0 | 7.0 | 9.0 | 4.0 | 9.0 | 7.0 | 8.0 | 7.0 | 7.0 | 2.0 |
|  | .125 | 0.0 | 7.0 | 2.0 | 4.0 | 4.0 | 0.0 | 5.0 | 5.0 | 3.0 | 3.0 | 0.0 | 0.0 |
| 16 | 4.000 | 2.0 | — | 4.0 | 6.0 | 2.0 | 1.0 | 9.0 | 4.0 | — | — | — | — |
| 17 | .500 | 8.0 | 9.0 | 9.0 | 9.0 | 9.0 | 9.0 | 9.0 | 9.0 | 9.0 | 9.0 | 9.0 | 8.0 |
|  | .125 | 6.0 | 9.0 | 9.0 | 9.0 | 9.0 | 8.0 | 9.0 | 8.0 | 9.0 | 9.0 | 8.0 | 7.0 |
| 18 | 4.000 | 9.0 | — | 8.0 | 9.0 | 9.0 | 7.0 | 9.0 | 8.0 | — | — | — | — |
|  | .500 | 9.0 | 9.0 | 9.0 | 9.0 | 9.0 | 9.0 | 9.0 | 9.0 | 9.0 | 9.0 | 9.0 | 8.0 |
|  | .125 | 2.0 | 9.0 | 9.0 | 9.0 | 9.0 | 9.0 | 9.0 | 9.0 | 9.0 | 9.0 | 9.0 | 7.0 |
| 19 | 4.000 | 8.0 | — | 8.0 | 8.0 | 9.0 | 8.0 | 9.0 | 8.0 | — | — | — | — |
|  | .500 | 2.2 | 7.0 | 8.0 | 7.0 | 6.0 | 5.5 | 9.0 | 8.0 | 9.0 | 7.0 | 5.0 | 5.0 |
|  | .125 | 0.4 | 0.0 | 0.0 | 0.0 | 0.0 | 1.7 | 0.0 | 0.0 | 0.0 | 0.0 | 0.0 | 0.0 |
| 20 | 4.000 | 9.0 | — | 8.0 | 9.0 | 9.0 | 8.0 | 9.0 | 9.0 | — | — | — | — |
|  | .500 | 8.5 | 9.0 | 9.0 | 9.0 | 8.5 | 9.0 | 8.5 | 9.0 | 9.0 | 8.0 | 7.5 | 7.0 |
|  | .125 | 9.0 | 9.0 | 7.0 | 7.0 | 9.0 | 8.0 | 9.0 | 8.0 | 5.0 | 7.0 | 9.0 | 6.0 |
| 21 | 4.000 | 9.0 | — | 8.0 | 9.0 | 9.0 | 9.0 | 9.0 | 9.0 | — | — | — | — |
|  | .500 | 8.5 | 9.0 | 9.0 | 9.0 | 9.0 | 8.3 | 9.0 | 9.0 | 8.5 | 9.0 | 9.0 | 7.5 |
|  | .125 | 5.5 | 8.5 | 8.0 | 3.0 | 9.0 | 6.0 | 8.5 | 8.0 | 4.0 | 5.5 | 8.5 | 4.0 |

TABLE I-continued

| | | Preemergence Herbicidal Evaluation of Test Compounds | | | | | | | | | | |
|---|---|---|---|---|---|---|---|---|---|---|---|---|
| Compound No. | Rate (kg/ha) | Barn-yardgr | Foxtail Sp | Wild oats | Quack grass | Fld Bindwd | Mrnglry Sp | Wild mustd | Velvet-leaf | Wht Fenman | Corn field | Cotton | Soybean |
| 22 | 4.000 | 8.0 | — | 8.0 | 9.0 | 9.0 | 8.0 | 9.0 | 8.0 | — | — | — | — |
|  | .500 | 3.3 | 8.0 | 8.0 | 5.0 | 9.0 | 4.0 | 9.0 | 8.0 | 2.0 | 3.0 | 8.0 | 1.0 |
|  | .125 | 0.0 | 0.0 | 0.0 | 0.0 | 2.0 | 0.0 | 7.0 | 5.0 | 0.0 | 0.0 | 2.0 | 0.0 |
| 23 | 4.000 | 9.0 | — | 8.0 | 9.0 | 9.0 | 8.0 | 9.0 | 9.0 | — | — | — | — |
|  | .500 | 8.0 | 9.0 | 9.0 | 9.0 | 9.0 | 7.7 | 9.0 | 8.5 | 8.5 | 9.0 | 9.0 | 7.5 |
|  | .125 | 4.0 | 7.5 | 7.5 | 4.5 | 9.0 | 5.3 | 9.0 | 8.5 | 3.5 | 7.0 | 8.5 | 5.0 |
| 24 | .500 | 0.0 | 8.0 | 3.0 | 2.0 | 4.0 | 2.0 | 7.0 | 7.0 | 1.0 | 1.0 | 6.0 | 3.0 |
| 25 | .500 | 9.0 | 9.0 | 8.0 | 9.0 | 9.0 | 8.0 | 9.0 | 9.0 | 9.0 | 9.0 | 8.0 | 1.0 |
|  | .125 | 8.0 | 8.0 | 7.0 | 8.0 | 9.0 | 7.0 | 9.0 | 9.0 | 2.0 | 5.0 | 7.0 | 1.0 |
| 26 | 4.000 | 7.0 | — | 8.0 | 9.0 | 9.0 | 6.0 | 9.0 | 7.0 | — | — | — | — |
|  | .500 | 4.0 | 6.0 | 0.0 | 0.0 | 4.0 | 0.0 | 8.0 | 3.0 | 0.0 | 0.0 | 0.0 | 0.0 |
| 27 | .500 | 9.0 | 9.0 | 6.0 | 9.0 | 9.0 | 8.0 | 9.0 | 8.0 | 7.0 | 9.0 | 8.0 | 2.0 |
|  | .125 | 7.0 | 9.0 | 2.0 | 4.0 | 9.0 | 1.0 | 8.0 | 7.0 | 3.0 | 3.0 | 6.0 | 0.0 |
| 28 | 4.000 | 8.0 | — | 6.0 | 6.0 | 9.0 | 6.0 | 8.0 | 7.0 | — | — | — | — |
|  | .500 | 7.0 | 7.0 | 0.0 | 0.0 | 9.0 | 0.0 | 8.0 | 7.0 | 0.0 | 1.0 | 2.0 | 0.0 |
|  | .125 | 0.0 | 0.0 | 0.0 | 0.0 | 0.0 | 0.0 | 1.0 | 0.0 | 0.0 | 0.0 | 0.0 | 0.0 |
| 29 | .500 | 9.0 | 9.0 | 7.0 | 9.0 | 9.0 | 7.0 | 9.0 | 8.0 | 8.0 | 7.0 | 8.0 | 2.0 |
|  | .125 | 7.0 | 8.0 | 2.0 | 5.0 | 9.0 | 2.0 | 8.0 | 7.0 | 3.0 | 3.0 | 8.0 | 0.0 |
| 30 | .500 | 2.0 | 6.0 | 2.0 | 2.0 | 8.0 | 2.0 | 7.0 | 7.0 | 1.0 | 4.0 | 3.0 | 3.0 |
| 31 | .500 | 0.0 | 4.0 | 0.0 | 0.0 | 4.0 | 2.0 | 9.0 | 8.0 | 0.0 | 0.0 | 0.0 | 0.0 |
|  | .125 | 0.0 | 0.0 | 0.0 | 0.0 | 0.0 | 0.0 | 4.0 | 0.0 | 0.0 | 0.0 | 0.0 | 0.0 |
| 32 | 4.000 | 9.0 | — | 9.0 | 8.0 | 9.0 | 6.0 | 9.0 | 6.0 | — | — | — | — |
| 33 | 4.000 | 8.0 | — | 7.0 | 9.0 | 9.0 | 8.0 | 9.0 | 6.0 | — | — | — | — |
|  | .500 | 0.0 | 0.0 | 1.0 | 6.0 | 1.0 | 2.0 | 8.0 | 5.0 | 1.0 | 7.0 | 4.0 | 0.0 |
| 34 | 4.000 | 8.0 | — | 7.0 | 9.0 | 9.0 | 6.0 | 9.0 | 7.0 | — | — | — | — |
|  | .500 | 8.0 | 9.0 | 9.0 | 9.0 | 9.0 | 9.0 | 9.0 | 9.0 | 9.0 | 8.0 | 9.0 | 7.0 |
|  | .125 | 6.0 | 9.0 | 9.0 | 8.0 | 8.0 | 7.0 | 9.0 | 8.0 | 8.0 | 8.0 | 8.0 | 3.0 |
| 35 | .500 | 7.0 | 8.0 | 9.0 | 6.0 | 9.0 | 8.0 | 9.0 | 9.0 | 6.0 | 9.0 | 7.0 | 7.0 |
|  | .125 | 0.0 | 7.0 | 3.0 | 2.0 | 9.0 | 4.0 | 8.0 | 7.0 | 0.0 | 2.0 | 2.0 | 1.0 |
| 36 | .500 | 4.0 | 9.0 | 8.0 | 9.0 | 9.0 | 7.0 | 9.0 | 8.0 | 9.0 | 9.0 | 7.0 | 2.0 |
|  | .125 | 0.0 | 4.0 | 4.0 | 4.0 | 2.0 | 0.0 | 5.0 | 3.0 | 6.0 | 2.0 | 4.0 | 0.0 |

EXAMPLE 5

Postemergence herbicidal evaluation of test compounds

The postemergence herbicidal activity of the compounds of the present invention is demonstrated by the following tests, wherein a variety of monocotyledonous and dicotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.125 kg to 4.0 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 4 above. The data obtained are recorded in Table II below. The compounds evaluated are reported by compound number given in Example 4.

TABLE II

| | | Postemergence Herbicidal Evaluation of Test Compounds | | | | | | | | | | |
|---|---|---|---|---|---|---|---|---|---|---|---|---|
| Compound No. | Rate (kg/ha) | Barn-yardgr | Foxtail Sp | Wild oats | Quack grass | Fld Bindwd | Mrnglry Sp | Wild mustd | Velvet-leaf | Wht Fenman | Corn field | Cotton | Soybean |
| 1 | 4.000 | 9.0 | — | 9.0 | 9.0 | 9.0 | 9.0 | 9.0 | 9.0 | — | — | — | — |
|  | .500 | 9.0 | 9.0 | 9.0 | 9.0 | 9.0 | 9.0 | 9.0 | 9.0 | 9.0 | 9.0 | 9.0 | 9.0 |
|  | .125 | 8.0 | 9.0 | 9.0 | 8.0 | 9.0 | 9.0 | 9.0 | 9.0 | 9.0 | 9.0 | 8.0 | 7.0 |
| 2 | 4.000 | 9.0 | — | 8.0 | 0.0 | 6.0 | 6.0 | 9.0 | 8.0 | — | — | — | — |
|  | .500 | 7.4 | 9.0 | 9.0 | 6.0 | 7.0 | 7.7 | 9.0 | 7.0 | 9.0 | 9.0 | 8.0 | 7.0 |
|  | .125 | 4.4 | 8.0 | 9.0 | 4.0 | 6.0 | 6.3 | 9.0 | 8.0 | 8.0 | 9.0 | 8.0 | 7.0 |
| 3 | 4.000 | 9.0 | — | 9.0 | 9.0 | 9.0 | 9.0 | 9.0 | 9.0 | — | — | — | — |
|  | .500 | 9.0 | 9.0 | 9.0 | 9.0 | 9.0 | 9.0 | 9.0 | 9.0 | 9.0 | 9.0 | 9.0 | 8.0 |
|  | .125 | 7.0 | 9.0 | 9.0 | 8.0 | 8.0 | 9.0 | 9.0 | 9.0 | 9.0 | 9.0 | 9.0 | 8.0 |
| 4 | .500 | 9.0 | 9.0 | 9.0 | 8.0 | 9.0 | 9.0 | 9.0 | 9.0 | 9.0 | 9.0 | 9.0 | 8.0 |
|  | .125 | 9.0 | 9.0 | 8.0 | 3.0 | 8.0 | 9.0 | 9.0 | 9.0 | 9.0 | 8.0 | 7.0 | 3.0 |
| 5 | .500 | 8.0 | 9.0 | 9.0 | 4.0 | 9.0 | 9.0 | 9.0 | 9.0 | 9.0 | 9.0 | 7.0 | 7.0 |
|  | .125 | 8.0 | 9.0 | 6.0 | 2.0 | 9.0 | 8.0 | 9.0 | 9.0 | 7.0 | 9.0 | 7.0 | 7.0 |
| 6 | 4.000 | 9.0 | — | 9.0 | 1.0 | 8.0 | 6.0 | 9.0 | 8.0 | — | — | — | — |
|  | .500 | 8.3 | 9.0 | 9.0 | 3.5 | 9.0 | 8.7 | 9.0 | 9.0 | 8.5 | 8.5 | 9.0 | 7.0 |
|  | .125 | 6.5 | 8.0 | 8.0 | 1.0 | 7.5 | 7.3 | 7.0 | 8.0 | 7.0 | 6.5 | 8.5 | 4.5 |
| 7 | .500 | 8.0 | 9.0 | 8.0 | 0.0 | 8.0 | 7.0 | 8.0 | 9.0 | 9.0 | 8.0 | 8.0 | 7.0 |
|  | .125 | 8.0 | 8.0 | 8.0 | 0.0 | 2.0 | 7.0 | 7.0 | 8.0 | 6.0 | 5.0 | 8.0 | 0.0 |
| 8 | .500 | 7.0 | 8.0 | 3.0 | 9.0 | 9.0 | 5.0 | 9.0 | 9.0 | 9.0 | 9.0 | 4.0 | 2.0 |
|  | .125 | 4.0 | 2.0 | 2.0 | 4.0 | 9.0 | 4.0 | 9.0 | 3.0 | 8.0 | 8.0 | 3.0 | 0.0 |
| 9 | .500 | 4.0 | 7.0 | 4.0 | 7.0 | 9.0 | 4.0 | 9.0 | 6.0 | 2.0 | 3.0 | 0.0 | 0.0 |
|  | .125 | 2.0 | 2.0 | 2.0 | 0.0 | 4.0 | 0.0 | 8.0 | 0.0 | 0.0 | 0.0 | 0.0 | 0.0 |
| 10 | 4.000 | 9.0 | — | 9.0 | 7.0 | 9.0 | 9.0 | 9.0 | 9.0 | — | — | — | — |
|  | .500 | 9.0 | 9.0 | 9.0 | 4.0 | 8.0 | 8.0 | 9.0 | 9.0 | 9.0 | 9.0 | 9.0 | 3.0 |

TABLE II-continued

Postemergence Herbicidal Evaluation of Test Compounds

| Compound No. | Rate (kg/ha) | Barn-yardgr | Foxtail Sp | Wild oats | Quack grass | Fld Bindwd | Mrnglry Sp | Wild mustd | Velvet-leaf | Wht Fenman | Corn field | Cotton | Soybean |
|---|---|---|---|---|---|---|---|---|---|---|---|---|---|
| | .125 | 8.0 | 9.0 | 8.0 | 2.0 | 8.0 | 6.0 | 9.0 | 8.0 | 6.0 | 7.0 | 9.0 | 1.0 |
| 11 | 4.000 | 9.0 | — | 9.0 | 4.0 | 9.0 | 8.0 | 9.0 | 9.0 | — | — | — | — |
| | .500 | 8.0 | 8.0 | 6.5 | 3.0 | 7.0 | 6.0 | 9.0 | 7.5 | 6.0 | 7.5 | 7.0 | 0.5 |
| | .125 | 6.5 | 7.0 | 4.0 | 1.0 | 5.5 | 2.0 | 8.0 | 6.0 | 3.0 | 2.5 | 5.5 | 0.5 |
| 12 | .500 | 8.0 | 8.0 | 6.0 | 0.0 | 8.0 | 4.0 | 8.0 | 7.0 | 2.0 | 2.0 | 7.0 | 0.0 |
| | .125 | 4.0 | 2.0 | 4.0 | 0.0 | 2.0 | 0.0 | 4.0 | 0.0 | 1.0 | 2.0 | 2.0 | 0.0 |
| 13 | .500 | 8.0 | 9.0 | 7.0 | 4.0 | 9.0 | 6.0 | 9.0 | 8.0 | 7.0 | 6.0 | 4.0 | 1.0 |
| | .125 | 4.0 | 6.0 | 4.0 | 2.0 | 4.0 | 0.0 | 7.0 | 2.0 | 2.0 | 3.0 | — | 0.0 |
| 14 | .500 | 9.0 | 9.0 | 9.0 | 9.0 | 9.0 | 8.0 | 9.0 | 9.0 | 9.0 | 9.0 | 9.0 | 3.0 |
| | .125 | 7.0 | 9.0 | 5.0 | 8.0 | 7.0 | 8.0 | 9.0 | 9.0 | 8.0 | 9.0 | 9.0 | 2.0 |
| 15 | .500 | 2.0 | 9.0 | 9.0 | 8.0 | 9.0 | 7.0 | 9.0 | 9.0 | 9.0 | 9.0 | 8.0 | 0.0 |
| | .125 | 2.0 | 9.0 | 2.0 | 8.0 | 6.0 | 0.0 | 2.0 | 8.0 | 8.0 | 8.0 | 6.0 | 0.0 |
| 16 | 4.000 | 6.0 | — | 7.0 | 8.0 | 8.0 | 0.0 | 9.0 | 1.0 | — | — | — | — |
| 17 | .500 | 9.0 | 9.0 | 9.0 | 7.0 | 8.0 | 9.0 | 9.0 | 9.0 | 9.0 | 9.0 | 9.0 | 8.0 |
| | .125 | 5.0 | 8.0 | 5.0 | 6.0 | 9.0 | 9.0 | 9.0 | 9.0 | 8.0 | 9.0 | 8.0 | 7.0 |
| 18 | 4.000 | 9.0 | — | 9.0 | 8.0 | 9.0 | 9.0 | 9.0 | 9.0 | — | — | — | — |
| | .500 | 9.0 | 9.0 | 9.0 | 9.0 | 7.0 | 9.0 | 9.0 | 9.0 | 9.0 | 9.0 | 8.0 | 7.0 |
| | .125 | 7.0 | 8.0 | 7.0 | 7.0 | 5.0 | 6.0 | 9.0 | 9.0 | 9.0 | 9.0 | 7.0 | 5.0 |
| 19 | 4.000 | 9.0 | — | 4.0 | 0.0 | 2.0 | 6.0 | 8.0 | 8.0 | — | — | — | — |
| | .500 | 4.8 | 9.0 | 8.0 | 6.0 | 7.0 | 5.0 | 8.0 | 8.0 | 8.0 | 7.0 | 7.0 | 3.0 |
| | .125 | 2.2 | 0.0 | 5.0 | 4.0 | 2.0 | 0.7 | 8.0 | 7.0 | 2.0 | 2.0 | 7.0 | 1.0 |
| 20 | 4.000 | 6.0 | — | 6.0 | 0.0 | 4.0 | 4.0 | 8.0 | 5.0 | — | — | — | — |
| | .500 | 9.0 | 9.0 | 8.0 | 7.0 | 7.5 | 6.5 | 9.0 | 9.0 | 8.0 | 9.0 | 7.0 | 7.0 |
| | .125 | 9.0 | 9.0 | 7.0 | 4.0 | 5.0 | 8.0 | 9.0 | 9.0 | 7.0 | 8.0 | 7.0 | 4.0 |
| 21 | 4.000 | 9.0 | — | 9.0 | 2.0 | 7.0 | 6.0 | 9.0 | 8.0 | — | — | — | — |
| | .500 | 9.0 | 9.0 | 9.0 | 2.0 | 9.0 | 8.5 | 9.0 | 9.0 | 9.0 | 9.0 | 9.0 | 7.0 |
| | .125 | 8.3 | 9.0 | 9.0 | 2.0 | 7.0 | 7.3 | 9.0 | 8.0 | 6.5 | 4.5 | 8.5 | 3.5 |
| 22 | 4.000 | 9.0 | — | 9.0 | 2.0 | 7.0 | 6.0 | 8.0 | 9.0 | — | — | — | — |
| | .125 | 4.0 | 2.0 | 6.0 | 0.0 | 6.0 | 8.0 | 7.0 | 0.0 | 2.0 | 2.0 | 8.0 | 8.0 |
| 23 | 4.000 | 9.0 | — | 9.0 | 2.0 | 7.0 | 6.0 | 9.0 | 9.0 | — | — | — | — |
| | .500 | 9.0 | 9.0 | 8.5 | 6.5 | 9.0 | 8.7 | 9.0 | 9.0 | 8.5 | 8.5 | 8.0 | 6.5 |
| | .125 | 7.5 | 8.0 | 8.0 | 3.0 | 5.0 | 6.0 | 7.5 | 7.5 | 8.0 | 3.0 | 7.5 | 1.5 |
| 24 | .500 | 8.0 | 8.0 | 2.0 | 0.0 | 2.0 | 6.0 | 6.0 | 7.0 | 2.0 | 2.0 | 6.0 | 0.0 |
| | .125 | 2.0 | 6.0 | 0.0 | 0.0 | 0.0 | 0.0 | 0.0 | 0.0 | 0.0 | 0.0 | 0.0 | 0.0 |
| 25 | .500 | 9.0 | 9.0 | 7.0 | 8.0 | 7.0 | 7.0 | 9.0 | 8.0 | 9.0 | 8.0 | 7.0 | 0.0 |
| | .125 | 8.0 | 9.0 | 2.0 | 4.0 | 4.0 | 4.0 | 9.0 | 7.0 | 3.0 | 3.0 | 3.0 | 0.0 |
| 26 | 4.000 | 9.0 | — | 4.0 | 6.0 | 9.0 | 1.0 | 9.0 | 4.0 | — | — | — | — |
| | .500 | 6.0 | 8.0 | 4.0 | 2.0 | 8.0 | 3.0 | 9.0 | 4.0 | 0.0 | 0.0 | 4.0 | 0.0 |
| | .125 | 0.0 | 0.0 | 0.0 | 0.0 | 0.0 | 0.0 | 3.0 | 0.0 | 0.0 | 0.0 | 0.0 | 0.0 |
| 27 | .500 | 9.0 | 8.0 | 6.0 | 6.0 | 7.0 | 7.0 | 8.0 | 8.0 | 6.0 | 6.0 | 7.0 | 0.0 |
| | .125 | 8.0 | 7.0 | 2.0 | 4.0 | 4.0 | 0.0 | 6.0 | 6.0 | 1.0 | 1.0 | 2.0 | 0.0 |
| 28 | 4.000 | 7.0 | — | 5.0 | 4.0 | 4.0 | 9.0 | 5.0 | — | — | — | — | — |
| | .500 | 8.0 | 7.0 | 2.0 | 1.0 | 7.0 | 2.0 | 7.0 | 4.0 | 3.0 | 2.0 | 6.0 | 0.0 |
| | .125 | 2.0 | 5.0 | 0.0 | 0.0 | 2.0 | 0.0 | 3.0 | 0.0 | 0.0 | 0.0 | 0.0 | 0.0 |
| 29 | .500 | 9.0 | 9.0 | 8.0 | 8.0 | 9.0 | 4.0 | 9.0 | 7.0 | 8.0 | 9.0 | 7.0 | 1.0 |
| | .125 | 7.0 | 7.0 | 4.0 | 0.0 | 2.0 | 0.0 | 4.0 | 2.0 | 2.0 | 3.0 | 4.0 | 0.0 |
| 30 | .500 | 2.0 | 4.0 | 0.0 | 0.0 | 4.0 | 0.0 | 8.0 | 0.0 | 0.0 | 0.0 | 0.0 | 0.0 |
| 31 | .500 | 2.0 | 4.0 | 0.0 | 2.0 | 4.0 | 0.0 | 8.0 | 7.0 | 1.0 | 2.0 | 3.0 | 0.0 |
| | .125 | 0.0 | 2.0 | 0.0 | 0.0 | 0.0 | 0.0 | 6.0 | 2.0 | 0.0 | 0.0 | 0.0 | 0.0 |
| 32 | 4.000 | 8.0 | — | 9.0 | 9.0 | 9.0 | 2.0 | 9.0 | 3.0 | — | — | — | — |
| 33 | 4.000 | 9.0 | — | 8.0 | 0.0 | 4.0 | 6.0 | 8.0 | 5.0 | — | — | — | — |
| | .500 | 2.3 | 7.0 | 4.0 | 2.0 | 0.0 | 0.0 | 8.0 | 2.0 | 2.0 | 7.0 | 7.0 | 0.0 |
| | .125 | 0.0 | 0.0 | 2.0 | 0.0 | 0.0 | 0.0 | 8.0 | 2.0 | 0.0 | 6.0 | 6.0 | 0.0 |
| 34 | 4.000 | 9.0 | — | 9.0 | 9.0 | 9.0 | 7.0 | 9.0 | 9.0 | — | — | — | — |
| | .500 | 9.0 | 9.0 | 9.0 | 8.0 | 9.0 | 9.0 | 9.0 | 9.0 | 9.0 | 9.0 | 9.0 | 8.0 |
| | .125 | 4.0 | 8.0 | 8.0 | 8.0 | 8.0 | 9.0 | 9.0 | 9.0 | — | — | 8.0 | 6.0 |
| 35 | .500 | 9.0 | 9.0 | 8.0 | 7.0 | 9.0 | 9.0 | 9.0 | 9.0 | 9.0 | 9.0 | 8.0 | 8.0 |
| | .125 | 7.0 | 8.0 | 7.0 | 2.0 | 7.0 | 2.0 | 9.0 | 9.0 | 6.0 | 8.0 | 6.0 | 4.0 |
| 36 | .500 | 7.0 | 9.0 | 4.0 | 8.0 | 4.0 | 6.0 | 9.0 | 8.0 | 9.0 | 9.0 | 7.0 | 3.0 |
| | .125 | 4.0 | 8.0 | 2.0 | 7.0 | 4.0 | 2.0 | 7.0 | 7.0 | 7.0 | 8.0 | 7.0 | 1.0 |

We claim:

1. A compound having the structure

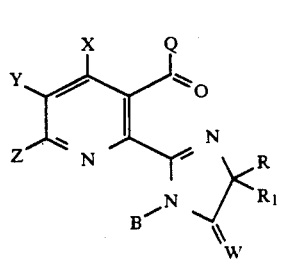

(I)

wherein
R is $C_1-C_4$ alkyl;
$R_1$ is $C_1-C_4$ alkyl or $C_3-C_6$ cycloalkyl; and when R and $R_1$ are taken together with the carbon to which they are attached they may represent $C_3-C_6$ cycloalkyl optionally substituted with methyl;
Q is

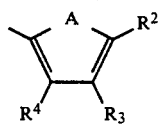

$R_2$, $R_3$ and $R_4$ are each independently hydrogen, halogen, $C_1$-$C_4$ alkyl, $C_1$-$C_4$ alkoxy, $C_1$-$C_4$ haloalkoxy or phenyl optionally substituted with one or two halogen atoms, $C_1$-$C_4$ alkyl or haloalkyl groups or $C_1$-$C_4$ alkoxy or haloalkoxy groups;

A is O or S;

B is hydrogen, $COR_6$ or $SO_2R_7$;

$R_6$ is $C_1$-$C_{11}$ alkyl, chloromethyl or phenyl optionally substituted with one chloro, one nitro or one methoxy group;

$R_7$ is $C_1$-$C_4$ alkyl or phenyl optionally substituted with one methyl group;

W is O or S;

X is hydrogen, halogen or methyl;

Y and Z are each independently hydrogen, halogen, $C_1$-$C_6$ alkyl, $C_1$-$C_4$ alkoxymethyl, $C_1$-$C_6$ alkoxy, $C_1$-$C_4$ alkylthio, phenoxy, $C_1$-$C_4$ haloalkyl, nitro, cyano, $C_1$-$C_4$ alkylsulfonyl or phenyl optionally substituted with one $C_1$-$C_4$ alkyl, $C_1$-$C_4$ alkoxy or halogen;

or when R and $R_1$ are not the same, the optical isomers thereof.

2. The compound according to claim 1 having the structure

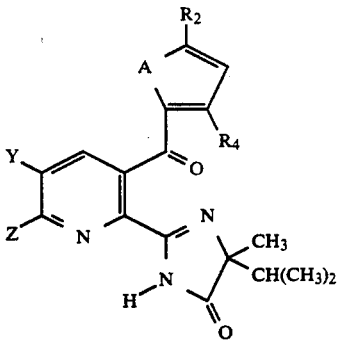

wherein $R_2$ and $R_4$ are independently hydrogen, halogen, $C_1$-$C_4$ alkyl, $C_1$-$C_4$ alkoxy, or $C_1$-$C_4$ haloalkoxy.

3. The compound according to claim 1 2-[3-(2-furoyl)-2-pyridyl]-4-isopropyl-4-methyl-2-imidazolin-5-one.

4. The compound according to claim 1 2-[3-(2-furoyl)-5-methyl-2-pyridyl]-4-isopropyl-4-methyl-2-imidazolin-5-one.

5. A method for controlling undesirable plant species which comprises applying to the foliage of said plants or to the soil or water containing seeds or other propagating organs thereof, a herbicidally effective amount of a compound as described in claim 1.

6. The method according to claim 5 wherein the compound is selected from the group consisting of 2-[3-(2-furoyl)-2-pyridyl]-4-isopropyl-4methyl-2-imidazolin-5-one; and 2-[3-(2-furoyl)-5-methyl-2-pyridyl]-4-isopropyl-4-methyl-2-imidazolin-5-one.

7. The method according to claim 5 which comprises applying said compound to the foliage of said plants at a rate of about 0.016 kg/ha to 4.0 kg/ha.

8. The method according to claim 5 which comprises applying said compound to the soil or water containing seeds or other propagating organs of said plants at a rate of about 0.016 kg/ha to 4.0 kg/ha.

9. A herbicidal composition which comprises an inert solid or liquid diluent and a herbicidally effective amount of a compound as described in claim 1.

* * * * *